United States Patent
Kawai (10) Patent No.: US 10,058,233 B2
(45) Date of Patent: Aug. 28, 2018

(54) INSERTION APPARATUS WITH TORQUE LIMIT DETERMINING SECTION

(71) Applicant: OLYMPUS CORPORATION, Tokyo (JP)

(72) Inventor: Toshimasa Kawai, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/294,087

(22) Filed: Oct. 14, 2016

(65) Prior Publication Data

US 2017/0027417 A1 Feb. 2, 2017

Related U.S. Application Data

(63) Continuation of application No. PCT/JP2015/063896, filed on May 14, 2015.

(30) Foreign Application Priority Data

Jul. 16, 2014 (JP) .................................. 2014-146068

(51) Int. Cl.
*A61B 1/06* (2006.01)
*A61B 1/00* (2006.01)
*A61B 1/04* (2006.01)

(52) U.S. Cl.
CPC ........ *A61B 1/0016* (2013.01); *A61B 1/00045* (2013.01); *A61B 1/00154* (2013.01);
(Continued)

(58) Field of Classification Search
CPC .............. A61B 1/0016; A61B 1/00045; A61B 1/00154; A61B 1/00156
(Continued)

(56) References Cited

U.S. PATENT DOCUMENTS

2005/0272976 A1* 12/2005 Tanaka ............... A61B 1/00073
600/114
2007/0167684 A1* 7/2007 Toyama ............... A61B 1/0055
600/128

(Continued)

FOREIGN PATENT DOCUMENTS

CN 103402416 A 11/2013
EP 1972257 A1 9/2008
(Continued)

OTHER PUBLICATIONS

International Search Report dated Aug. 4, 2015 issued in PCT/JP2015/063896.
(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An insertion apparatus includes an inserting section, a rotary cylinder, a motor, motor control section, a moving average calculating section, and a torque limit determining section. The inserting section is formed along a longitudinal axis. The rotary cylinder is provided to be rotatable around a longitudinal axis of the inserting section. The motor rotates the rotary cylinder. The motor control section supplies a motor current to drive the motor. The moving average calculating section calculates an average of the motor current within a predetermined period, after the motor starts up. The torque limit determining section determines whether torque of the motor is in a limit state by comparing a calculating result by the moving average calculating section with a predetermined torque limit set value, at timing except startup of the motor.

4 Claims, 8 Drawing Sheets

(52) U.S. Cl.
CPC ...... *A61B 1/00156* (2013.01); *A61B 1/00006* (2013.01); *A61B 1/00039* (2013.01)

(58) Field of Classification Search
USPC ....... 600/109, 114, 117, 120, 121, 128, 137, 600/138, 145, 160, 161
See application file for complete search history.

(56) References Cited

U.S. PATENT DOCUMENTS

| | | | |
|---|---|---|---|
| 2011/0015786 A1 | 1/2011 | Kawai | |
| 2012/0197082 A1 | 8/2012 | Uchiyama et al. | |
| 2013/0041222 A1 | 2/2013 | Moriyama | |
| 2014/0094654 A1 | 4/2014 | Miyamoto | |
| 2014/0306638 A1* | 10/2014 | Wu | H02P 27/08 318/504 |

FOREIGN PATENT DOCUMENTS

| | | |
|---|---|---|
| JP | 2008-093029 A | 4/2008 |
| JP | 2008-272302 A | 11/2008 |
| JP | 2014-004268 A | 1/2014 |
| JP | 2014-068816 A | 4/2014 |

OTHER PUBLICATIONS

Japanese Office Action dated Mar. 1, 2016 issued in JP 2015-558678.
English translation of International Preliminary Report on Patentability dated Jan. 26, 2017 together with the Written Opinion received in related International Application No. PCT/JP2015/063896.
Extended Supplementary European Search Report dated Feb. 21, 2018 in European Patent Application No. 15 82 2297.6.
Chinese Office Action dated Jul. 3, 2017 in Chinese Patent Application No. 201580015559.4.

* cited by examiner

INSERTION APPARATUS WITH TORQUE LIMIT DETERMINING SECTION

CROSS-REFERENCE TO RELATED APPLICATIONS

This application is a Continuation Application of PCT Application No. PCT/JP2015/063896, filed May 14, 2015 and based upon and claiming the benefit of priority from the prior Japanese Patent Application No. 2014-146068, filed Jul. 16, 2014, the entire contents of both of which are incorporated herein by reference.

BACKGROUND OF THE INVENTION

1. Field of the Invention

The present invention relates to a rotary self-propelled insertion apparatus.

2. Description of the Related Art

An insertion apparatus which is called a rotary self-propelled type or the like is known. A rotary cylinder having a rotatable spiral convex portion called a spiral fin is provided around an inserting section of the rotary self-propelled type insertion apparatus. Such a rotary self-propelled insertion apparatus self-travels in a lumen by rotation of the rotary cylinder. Consequently, insertion of the insertion apparatus into the lumen is aided. This type of rotary self-propelled insertion apparatus is used in such an endoscope system as disclosed in, e.g., Jpn. Pat. Appln. KOKAI Publication No. 2008-93029.

For example, in case of the endoscope system, power to rotate the rotary cylinder is obtained by a motor provided in an operating section of the insertion apparatus. Further, the power generated by the motor is transmitted to the rotary cylinder through a torque shaft provided in the insertion apparatus. Consequently, the rotary cylinder is rotated.

BRIEF SUMMARY OF THE INVENTION

An insertion apparatus according to an aspect of the invention comprises: an insertion apparatus comprising: an inserting section which is formed along a longitudinal axis extending from a proximal end side toward a distal end side; a rotary cylinder which is provided to be rotatable around a longitudinal axis of the inserting section, and includes a spiral fin spirally provided along the longitudinal axis of the inserting section; a motor which rotates the rotary cylinder; a motor control section which supplies a motor current to drive the motor, and controls driving of the motor; and a torque limit determining section which determines whether torque of the motor is in a limit state by comparing a moving average of the motor current with a predetermined torque limit set value.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the drawings.

[First Embodiment]

Figure 1:
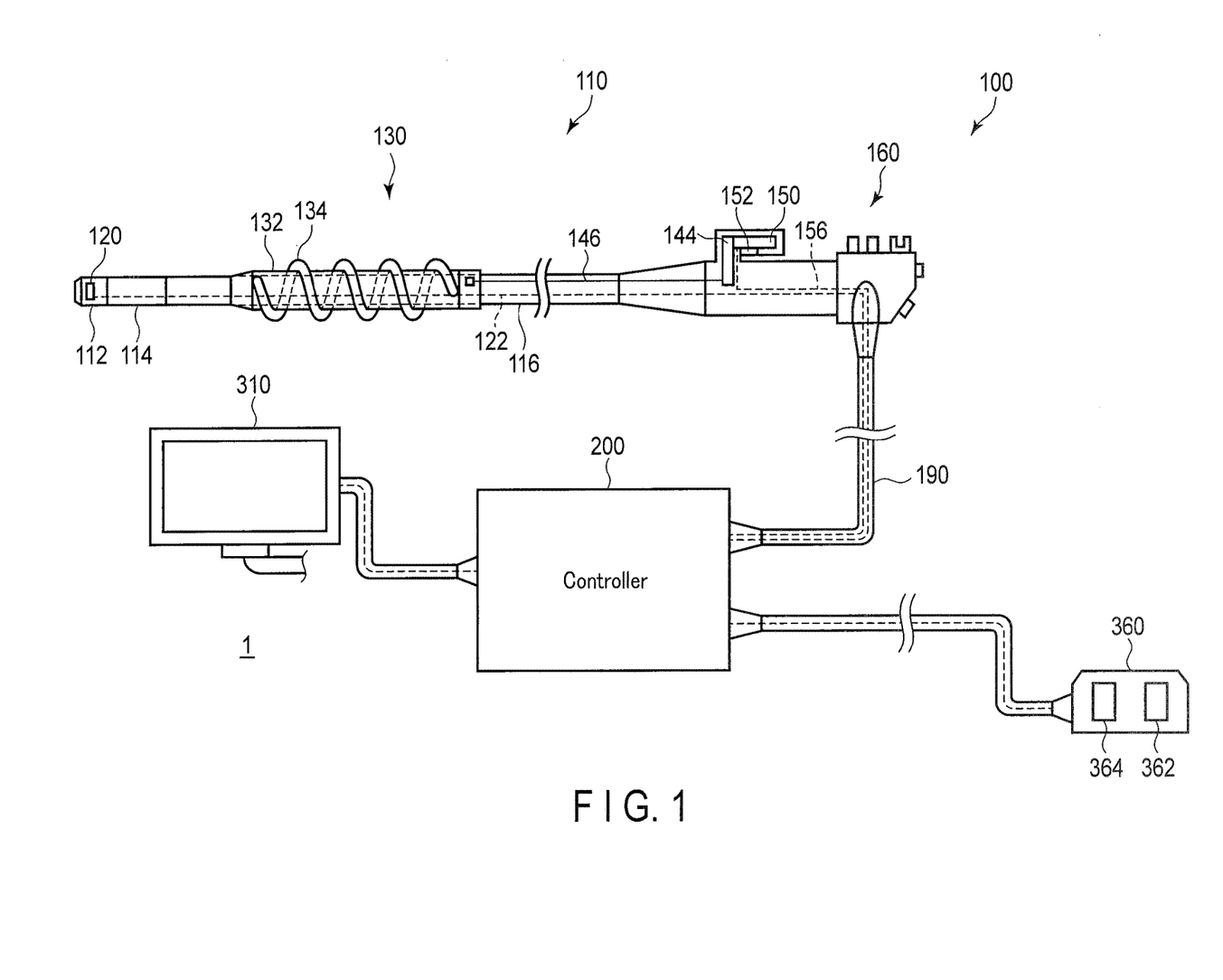
FIG. 1 is a view showing an outline of a configuration of an endoscope system as an example of an insertion apparatus according to each embodiment of the present invention.

A first embodiment according to the present invention will be first described. FIG. 1 is a view showing an outline of a configuration of an endoscope system as an example of an insertion apparatus 1 according to each embodiment of the present invention. As shown in this drawing, the insertion apparatus 1 includes an endoscope 100, a controller 200, a monitor 310, and an input section 360. The endoscope 100 is a rotary self-propelled endoscope, and includes an elongated inserting section 110 which configured to be inserted into an organism. Further, the endoscope 100 includes an operating section 160 to perform various kinds of operations of the endoscope 100. The operating section 160 is held by a user. Here, a side of a tip of the inserting section 110 will be referred to as a distal end side, and a side of the operating section 160 will be referred to as a proximal end side. Furthermore, a direction extending from the distal end side to the proximal end side of the inserting section 110 is determined as a longitudinal direction. The operating section 160 of the endoscope 100 is connected to the controller 200 through a universal cable 190.

The inserting section 110 includes a distal end hard section 112, a bending section 114, and a coiled hose section 116. The distal end hard section 112 is an endmost portion of the inserting section 110, and configured not to bend. The bending section 114 is a portion formed on the proximal end side of the distal end hard section 112, and configured to actively bend in correspondence with rotation of a non-illustrated operation knob provided to the operating section 160. The coiled hose section 116 is a portion formed on the proximal end side of the bending section 114, and passively bends by external force.

An imaging element 120 is provided to the distal end hard section 112. The imaging element 120 generates an image signal based on a subject image of, e.g., the distal end side of the inserting section 110. The image signal acquired by the imaging element 120 is transmitted to the controller 200 through a signal line 122 for image signals running through the inserting section 110 and the universal cable 190.

A power unit 130 which transmits driving power of a motor 150 included in the operating section 160 is disposed to the coiled hose section 116 of the inserting section 110. The power unit 130 includes a base tube 132 which is a rotary cylinder. The base tube 132 is rotatably attached around a longitudinal axis of the coiled hose section 116. The base tube 132 may be configured to be detachable from the coiled hose section 116. A spiral fin 134 is provided on an outer peripheral surface of the base tube 132. The spiral fin 134 is spirally provided around the longitudinal axis of the base tube 132.

Furthermore, the base tube 132 is connected to the motor 150 as an actuator provided to the operating section 160 through a gear in a gear box 144 and a torque shaft 146. The motor 150 is connected to the controller 200 through a signal line 156 for actuator current signals running through the operating section 160 and the universal cable 190.

When the motor 150 operates by an operation using the input section 360, its driving force is transmitted by the gear in the gear box 144 and the torque shaft 146. Consequently, the base tube 132 rotates around the longitudinal axis. With this rotation of the base tube 132, the spiral fin 134 also rotates.

In a state where the spiral fin 134 is in contact with a wall portion such as a lumen wall, when the spiral fin 134 rotates, propelling force which enables self-traveling of the inserting section 110 is produced. For example, in a small intestine or a large intestine, when the spiral fin 134 draws folds present on an inner wall of the small intestine or the large intestine, the propelling force acts on the inserting section 110. With this propelling force, the inserting section 110 self-travels. When the inserting section 110 self-travels, an inserting operation and a removal operation of the inserting section 110 performed by a user are aided. It is to be noted that, in the following description, a rotating direction of the motor 150 to enable self-traveling of the inserting section 110 toward the distal end side is determined as a forward rotating direction, and a rotating direction of the motor 150 to enable self-traveling of the inserting section 110 toward the proximal end side is determined as a reverse rotating direction.

An incremental encoder 152 is provided to the motor 150. The incremental encoder 152 generates an electrical signal (an encoder signal) corresponding to a rotational speed of the motor 150, and outputs the generated encoder signal to the controller 200 through a non-illustrated signal line running through the universal cable 190.

The monitor 310 is a general display element such as a liquid crystal display. The monitor 310 displays an endoscope image based on an image signal obtained by, e.g., the imaging element 120 under control of the controller 200.

The input section 360 includes, e.g., a footswitch. The footswitch includes a right foot pedal 362 and a left foot pedal 364. When the right foot pedal 362 is depressed by a user, it generates an instruction signal to rotate the motor 150 in a forward direction. Further, when the left foot pedal 364 is depressed by the user, it generates an instruction signal to rotate the motor 150 in a reverse direction. Furthermore, the right foot pedal 362 and the left foot pedal 364 are configured to generate signals having the same intensity corresponding to a level of depressing the pedals by the user, respectively. Moreover, the motor 150 is configured to rotate in the forward direction or in the reverse direction at a speed corresponding to depression of the right foot pedal 362 or the left foot pedal 364.

Figure 2:
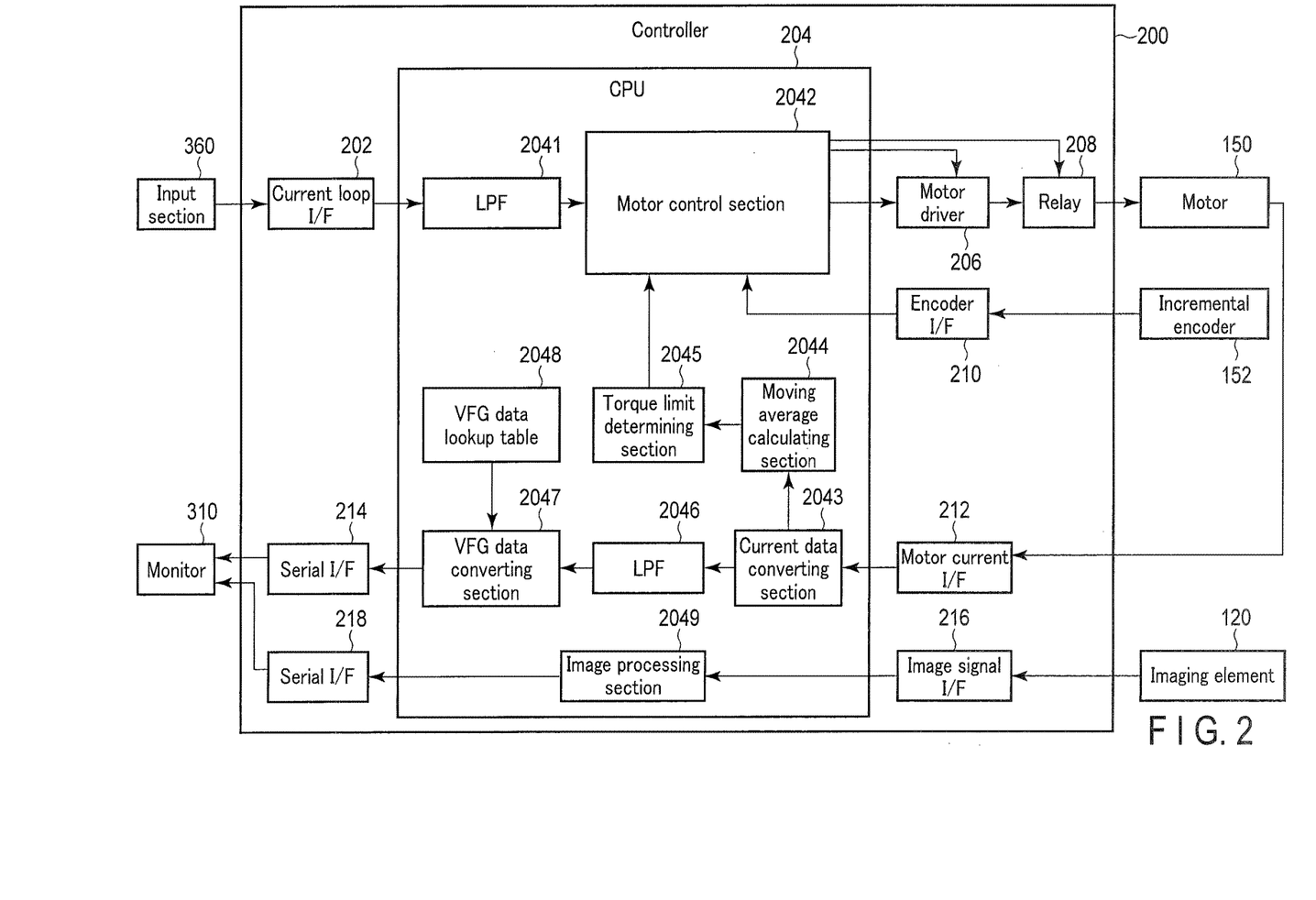
FIG. 2 is a block diagram showing a configuration of a controller.

The controller 200 controls the respective sections of the insertion apparatus 1. FIG. 2 is a block diagram showing a configuration of the controller 200. The controller 200 includes a current loop interface (I/F) 202, a CPU 204, a motor driver 206, a relay 208, an encoder I/F 210, a motor current I/F 212, a serial I/F 214, an image signal I/F 216, and a serial I/F 218.

The current loop I/F 202 is a serial interface to transmit an instruction signal generated by the input section 360 to an LPF 2041 of the CPU 204 on the basis of a current loop system.

The CPU 204 receives an instruction signal from the input section 360 and an encoder signal from the incremental encoder 152, and controls to drive the motor driver 206. Additionally, the CPU 204 processes an image signal from the imaging element 120, and displays an image based on the processed image signal in the monitor 310. Particulars of such a CPU 204 will now be described.

The motor driver 206 drives the motor 150 on the basis of a motor current supplied from a motor control section 2042 of the CPU 204. The motor driver 206 is constituted of, e.g., a driver amplification circuit. It is to be noted that the motor driver 206 may be configured to drive the motor 150 by PWM control.

The relay 208 is provided between the motor driver 206 and the motor 150, and electrically connects or electrically disconnects the motor driver 206 and the motor 150, i.e., the controller 200 and the motor 150 to or from each other on the basis of a relay switching signal from the motor control section 2042.

The encoder I/F 210 is an interface to transmit an encoder signal generated by the incremental encoder 152 to the motor control section 2042. The motor current I/F 212 is an interface to transmit a motor current supplied to the motor 150 to a current data converting section 2043 of the CPU 204. The serial I/F 214 is a serial interface to transmit VFG data obtained by a VFG (visual force gauge) data converting section 2047 of the CPU 204 to the monitor 310. The VFG data is data presented in the monitor 310 so that a variation in motor current value can be visually recognized. For example, the VFG data is configured to be superimposed on an observation image in the vicinity of an observation image screen of the monitor 310. The serial I/F 214 is a serial interface to transmit an image signal processed by an image processing section 2049 of the CPU 204 to the monitor 310.

Particulars of the CPU 204 will now be described. As shown in FIG. 2, the CPU 204 includes a low-pass filter (LPF) 2041, the motor control section 2042, the current data converting section 2043, a moving average calculating section 2044, a torque limit determining section 2045, an LPF 2046, the VFG (visual force gauge) data converting section 2047, a VFG data lookup table 2048, and the image processing section 2049.

The LPF 2041 performs low-pass filter processing to remove high-frequency noise in an instruction signal from the input section 360 input through the current loop I/F 202.

The motor control section 2042 performs a PI (proportional integral) speed control to the motor 150. That is, the motor control section 2042 generates a motor current instruction value so that the motor 150 rotates at a speed corresponding to the instruction signal, and inputs the generated motor current to the motor driver 206. Specifically, the motor control section 2042 generates the motor current instruction value on the basis of a difference signal between the instruction signal input through the LPF 2041 and the encoder signal input through the encoder I/F 210, and inputs the generated motor current to the motor driver 206. Further, the motor control section 2042 controls a state of the relay 208 in accordance with a determination result of the torque limit determining section 2045.

The current data converting section 2043 takes in the motor current, which is input through the motor current I/F 212, every predetermined sampling period, and converts a value of the taken-in motor current into a scale which can be used in the moving average calculating section 2044 and the VFG data converting section 2047.

Figure 3:
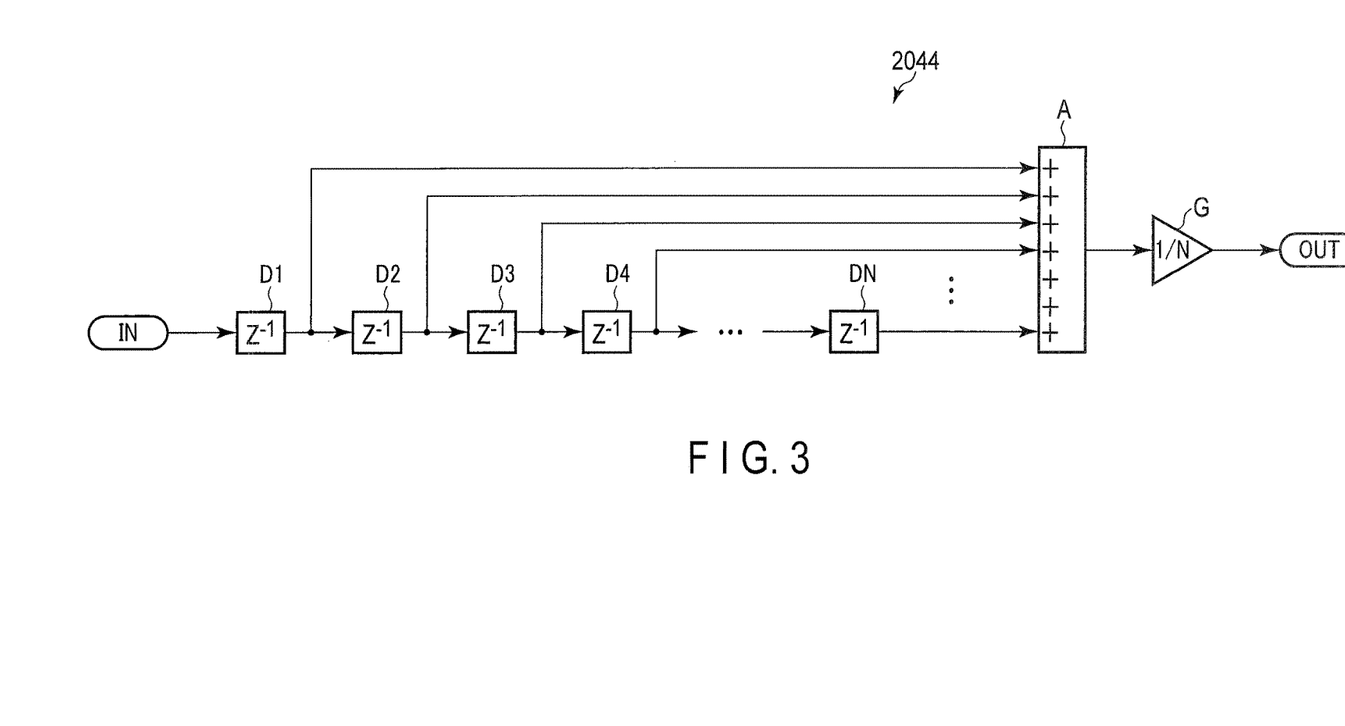
FIG. 3 is a view showing a circuit example of a moving average calculating section.

The moving average calculating section 2044 calculates an average value (a moving average of the motor current) of the motor current, which has been taken in by the current data converting section 2043, within a predetermined period. FIG. 3 shows a circuit example of the moving average calculating section 2044. As shown in FIG. 3, the moving average calculating section 2044 includes an input terminal IN, N delay units D1, D2, . . . , DN, an adder A, a gain unit G, and an output terminal OUT. Here, N is a natural number representing a sampling number. N is not restricted in particular as long as it is 2 or more.

Data of the motor current taken in by the current data converting section 2043 is input to the input terminal IN. The delay units D1 to DN delay the data of the motor current input through the input terminal IN every sampling period, respectively. N pieces of data of the motor current are simultaneously input to the adder A at a time point of a sampling period N by the delay units D1 to DN. The adder A adds the input N pieces of data of the motor current. The gain unit G multiplies an output (a sum total of the N pieces of data of the motor current) from the adder A by a gain of 1/N to calculate a moving average. With such a configuration, a value of the moving average obtained by the gain unit G is output from the output terminal OUT.

The torque limit determining section 2045 determines whether a torque limit is applied to the motor 150 by comparing the value of the moving average obtained by the moving average calculating section 2044 with a torque limit set value which is a predetermined current threshold value, and inputs a signal indicative of a determination result to the motor control section 2042. Here, the torque limit means processing to suppress torque of the motor 150.

The LPF 2046 performs low-pass filter processing to the data of the motor current input from the current data converting section 2043. The VFG data converting section 2047 converts the data of the motor current input from the LPF 2046 into VFG data by making reference to the VFG data lookup table 2048. The VFG data lookup table 2048 is a lookup table in which the data of the motor current is associated with the VFG data. The VFG data is display data which enables a user to recognize a magnitude of the motor current, i.e., a magnitude of torque of the motor 150.

The image processing section 2049 performs image processing to an image signal input through the image signal I/F 216. Furthermore, the image processing section 2049 inputs the processed image signal to the monitor 310 through the serial I/F 218, thereby displaying an endoscope image in the monitor 310.

Figure 4:
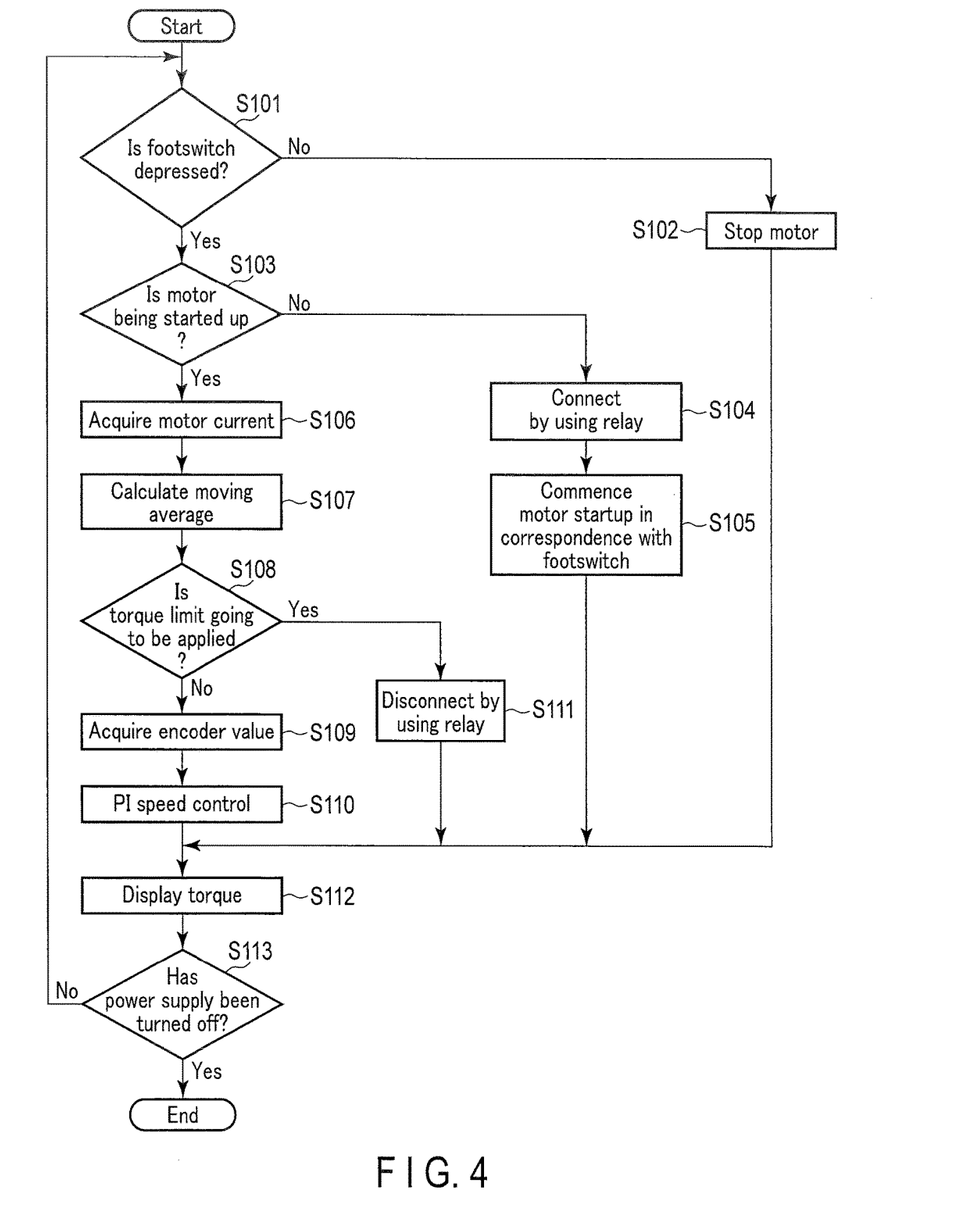
FIG. 4 is a flowchart showing an operation of motor control of an insertion apparatus.

An operation of the insertion apparatus 1 according to the first embodiment will now be described. FIG. 4 is a flowchart showing an operation of the motor control of the insertion apparatus 1. Processing shown in FIG. 4 is started when, for example, a power supply of the insertion apparatus 1 is turned on. It is to be noted that processing or the like to display an endoscope image based on an image signal obtained by the imaging element 120 in the monitor 310 is performed concurrently with the processing in FIG. 4.

At step S101, the motor control section 2042 determines whether the footswitch has been depressed, i.e., whether an instruction signal from the input section 360 has been input. At the step S101, when the footswitch is determined not to have been depressed, the processing advances to step S102. At the step S102, the motor control section 2042 stops the motor 150. For example, the motor control section 2042 stops supply of the motor current. Then, the processing advances to step S112. In the processing of the step S102, the motor 150 is stopped while performing the feedback control based on the PI speed control. Consequently, a rotational position of the motor 150 is maintained at a rotational position which is provided when a stop instruction is issued.

When the footswitch is determined to have been depressed at the step S101, the processing advances to step S103. At the step S103, the motor control section 2042 determines whether the motor 150 is being started up. Being started up here means that the motor 150 which is in, e.g., a state where a power supply of the insertion apparatus 1 is ON is not stopped.

When the motor 150 determined not to be being started up at the step S103, the processing advances to step S104. At the step S104, the motor control section 2042 inputs a relay switching signal to the relay 208 to achieve a connected state between the controller 200 and the motor 150. At step S105, the motor control section 2042 supplies the motor current corresponding to an instruction signal to the motor driver 206 to commence startup of the motor 150. Then, the processing advances to step S112.

When the motor 150 is determined to be being started up at the step S103, the processing advances to step S106. At the step S106, the moving average calculating section 2044 acquires data of the motor current supplied to the motor 150 through the motor current I/F 212 and the current data converting section 2043. Further, at step S107, the moving average calculating section 2044 calculates a moving average which is an average value of the most recent N pieces of data of the motor current. Then, at step S108, the torque limit determining section 2045 determines whether a torque limit is going to be applied to the motor torque 150. This determination is made by determining whether the moving average exceeds a torque limit set value. It is to be noted that when the N pieces of data of the motor current are not acquired, the processing of the step 107 is omitted. Moreover, at this time, it is determined that the torque limit is not going to be applied at the step S108.

When it is determined that the torque limit is not going to be applied at the step S108, i.e., when it is determined that the moving average does not exceed the torque limit set value, the processing proceeds to step S109. At the step S109, the motor control section 2042 acquires an encoder signal from the incremental encoder 152 through the encoder I/F 210. Further, at step S110, the motor control section 2042 performs the PI speed control. That is, the motor control section 2042 generates a motor current instruction value by PI control so that a difference between the instruction signal and the encoder signal becomes small. Then, the processing advances to step S112.

When it is determined that the torque limit is going to be applied at the step S108, the processing advances to step S111. At the step S111, the motor control section 2042 inputs a relay switching signal to the relay 208 to achieve a disconnected state between the controller 200 and the motor 150. Consequently, supply of the current to the motor 150 is interrupted, and the motor 150 is stopped. Then, the processing advances to step S112. In the processing of the step S111, since the motor 150 is disconnected from the controller 200 by the relay 208, the feedback control to maintain the rotational position of the motor 150 is not carried out. That is, the motor 150 is free from external force.

At the step S112, the VFG data converting section 2047 acquires VFG data corresponding to the data of the motor current from the VFG data lookup table 2048, and inputs the acquired VFG data to the monitor 310. The monitor 310 displays a state of torque of the current motor 150 on the basis of on the input VFG data.

FIG. 5A to FIG. 5D are views showing display examples of states of the torque. FIG. 5A to FIG. 5D show examples of displaying magnitudes of the torque by using a level meter. That is, in this example, 15 scale marks are set along a right direction (FORWARD) and a left direction (BACKWARD) with "0" indicating that the motor 150 is not rotating at the center. Here, "FORWARD" represents that the motor 150 is rotating in the forward direction. Additionally, "BACKWARD" represents that the motor 150 is rotating in the backward direction. A user can be aware of a state of the current motor 150 by visually confirming, in which direction, how many scale marks are turned on.

Figure 5A:
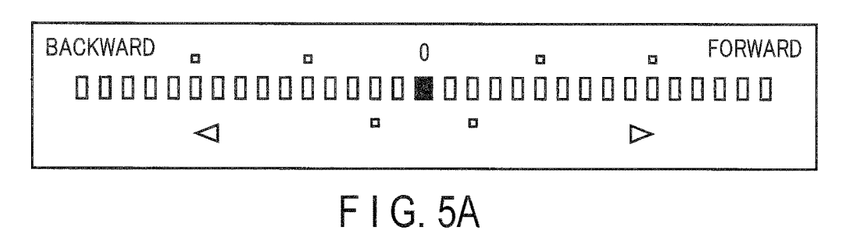
FIG. 5A is a first view showing a display example of a state of torque.
Figure 5B:
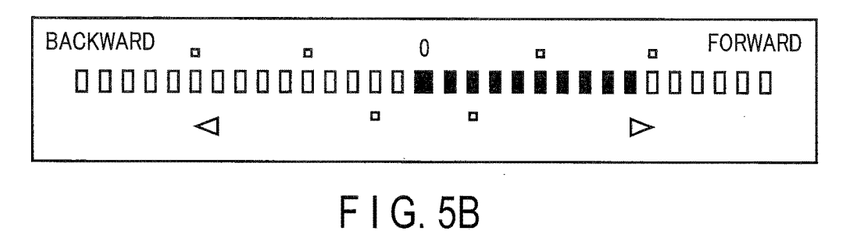
FIG. 5B is a second view showing a display example of a state of the torque.
Figure 5C:
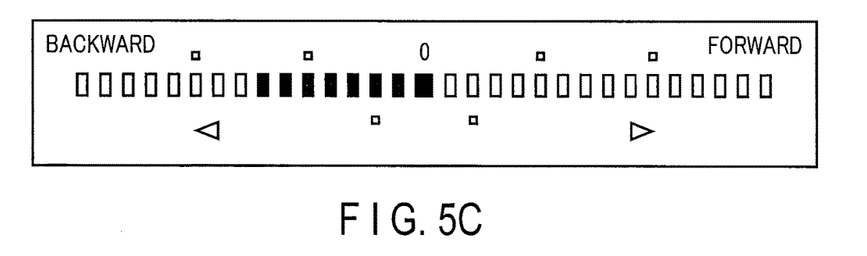
FIG. 5C is a third view showing a display example of a state of the torque.
Figure 5D:
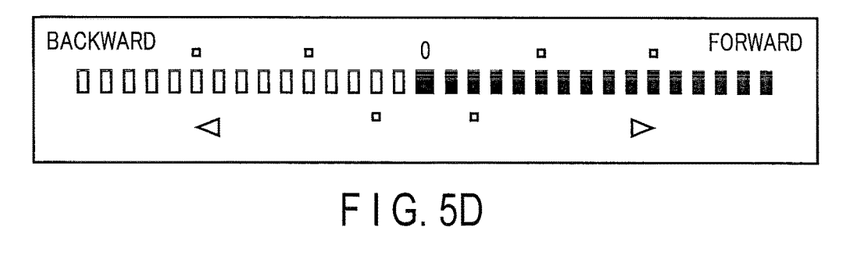
FIG. 5D is a fourth view showing a display example of a state of the torque.

For example, FIG. 5A is a display example when the motor current is not supplied to the motor 150, e.g., when a depressing amount of the footswitch is not enough to drive the motor 150. At this time, the scale mark at the position of "0" alone is ON. Consequently, the user can be aware that the motor 150 is not rotating. Further, FIG. 5B is a display example when the right foot pedal 362 of the footswitch is depressed. At this time, the scale marks in the direction "FORWARD" are turned on in correspondence with a magnitude of the motor current. Consequently, the user can be aware of a level of torque with which the motor 150 is rotating in the forward direction. Furthermore, FIG. 5C is a display example when the left foot pedal 364 of the footswitch is depressed. At this time, the scale marks in the direction "BACKWARD" are turned on in correspondence with a magnitude of the motor current. Consequently, the user can be aware of a level of torque with which the motor 150 is rotating in the backward direction. Moreover, FIG. 5D is a display example when the torque limit should be applied. At this time, all the scale marks in a direction along which rotation has been effected until now (e.g., FIG. 5D shows the direction of the forward direction) are displayed in a flashing manner. Consequently, the user can be aware that the torque limit has been applied.

It is to be noted that, in this embodiment, a state of torque is displayed in the monitor 310. On the other hand, a state of torque may be displayed in a display element different from the monitor 310.

Here, the description on FIG. 4 will be again given. After display of the torque state, at step S113, the motor control section 2042 determines whether the power supply of the insertion apparatus 1 has been turned off by the user. When the power supply of the insertion apparatus 1 is determined not to have been turned off at the step S113, the processing returns to the step S101. When the power supply of the insertion apparatus 1 is determined to have been turned off at the step S113, the processing of FIG. 4 is terminated.

Figure 6:
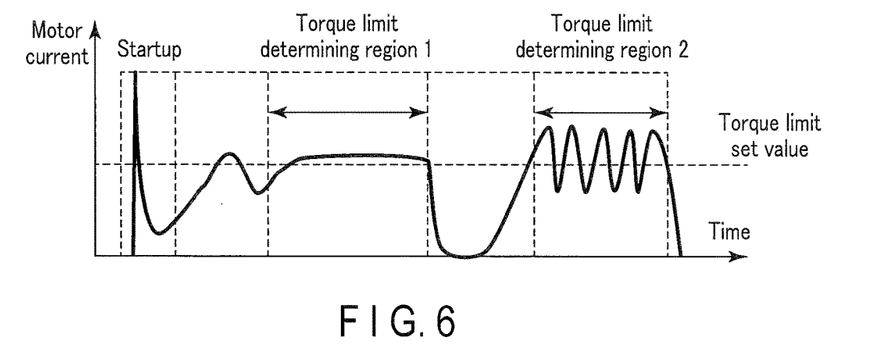
FIG. 6 is a view showing a torque limit determining region.

As described above, in this embodiment, whether the torque limit should be applied is determined on the basis of the moving average which is an average value of the motor current. When the moving average is compared with the torque limit set value, it is possible to determine not only a period of such a torque limit determining region 1 where the motor current continuously exceeds the torque limit set value as shown in FIG. 6 but also a period of a torque limit determining region 2 where the motor current oscillatorily changes in the vicinity of the torque limit set value. For example, when excessive rotational force is given to a lumen by rotation of the spiral fin 134, it is considered that an increase in torque of the motor 150 continues for a relatively long time. That is, in this embodiment, a period during which the excessive rotational force is given to the lumen by the rotation of the spiral fin 134 can be appropriately determined by determining whether the torque limit should be applied on the basis of the moving average which is an average value of the motor current.

Moreover, since an instantaneous value of the motor current is not compared with the torque limit set value, for example, when an increase in torque is determined for a quick moment alone, the motor 150 is not stopped. Consequently, the motor 150 can be prevented from being frequently stopped. Additionally, as shown in FIG. 6, a large motor current must be instantaneously flowed at the time of startup of the motor 150. In this embodiment, when the torque limit is prevented from being determined at the startup of the motor 150, the motor 150 can be properly started up.

It is to be noted that, in this embodiment, an average value of the motor current is calculated to determine whether the torque limit should be applied. On the other hand, for example, a square mean value, i.e., an effective value of the motor current may be calculated to determine whether the torque limit should be applied.

Further, in this embodiment, as processing when the torque limit is determined, the motor 150 is disconnected from the controller 200 by the relay 208. As described above, in the normal processing to stop the motor 150, feedback control to maintain a current rotational position of the motor 150 is performed. In this case, for example, in a situation where the spiral fin 134 is in contact with a lumen, there is a possibility that the motor 150 is stopped while keeping the excessive force given to the lumen. On the other hand, in this embodiment, when the motor 150 is set to be free from external force, the force given to the lumen can be eliminated.

It is to be noted that, in this embodiment, in a case where the motor 150 is disconnected from the controller 200 by the relay 208, when follow-up depression of the footswitch is then confirmed at the step S101, the connected state is achieved between the motor 150 and the controller 200, and driving of the motor 150 again begins.

[Second Embodiment]

A second embodiment according to the present invention will now be described. The second embodiment can provide the same effect as that of the first embodiment without using the relay 208. It is to be noted that, as a configuration of an insertion apparatus 1, one shown in FIG. 1 to FIG. 3 is applied except that the relay 208 is not required. Thus, a detailed description will be omitted. As regards an operation of motor control, switching of the relay 208 at the step S104 and the step S108 is substituted by an operation described below.

Figure 7:
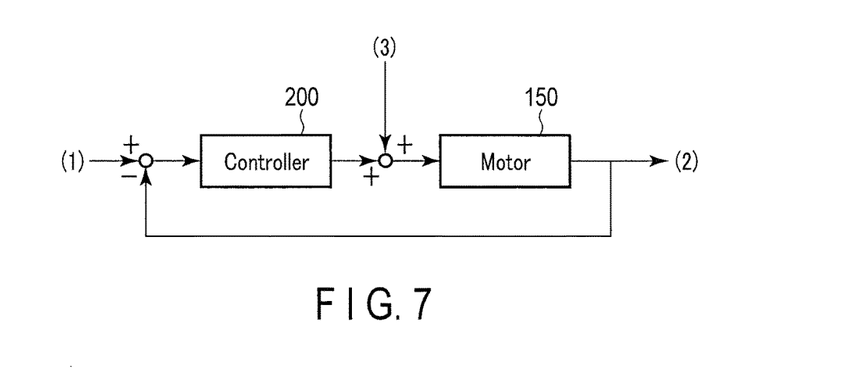
FIG. 7 is a block diagram showing a controller and a motor for explaining a second embodiment.

As described in the first embodiment, a controller 200 (a motor control section 2042) drives a motor 150 by PI speed control. At this time, the controller 200 and the motor 150 can be represented in such a block diagram as shown in FIG. 7. Here, (1) in FIG. 7 is an instruction value from an input section, and (2) denotes a rotational speed of the motor. Further, (3) represents that a load on a shaft of the motor is applied.

Figure 8A:
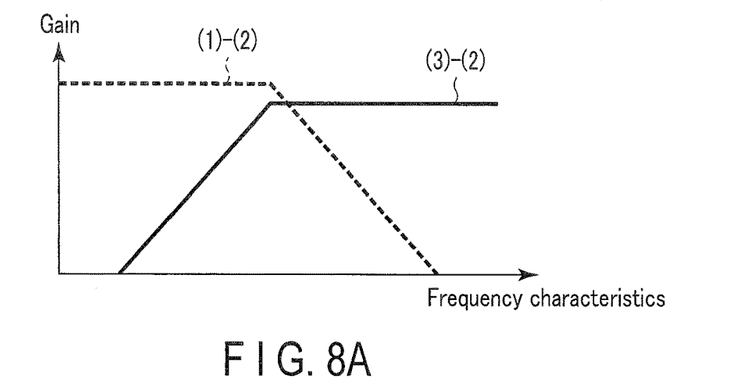
FIG. 8A is a first view showing switching of transmission characteristics.

As described above, when the torque limit is determined not to be applied, the motor control section 2042 performs the PI speed control so that a rotational speed of the motor 150 follows a depressing amount of a footswitch, i.e., a difference between an instruction signal and an encoder signal becomes small. Such PI speed control can be performed by setting transmission characteristics when the motor 150 is seen from an input section 360, i.e., transmission characteristics when (2) is seen from (1) in FIG. 7 as low-pass filter characteristic indicated by a broken line in FIG. 8A. It is to be noted that, at this time, transmission characteristics when the motor 150 is seen from a base tube 132 which is a rotary cylinder of a inserting section 110 are transmission characteristics when (2) is seen from (3) in FIG. 7, which are such high-pass filter characteristics as indicated by a solid line in FIG. 8A.

Figure 8B:
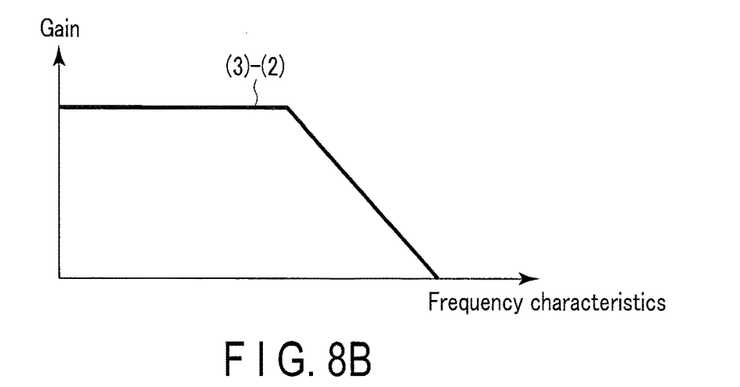
FIG. 8B is a second view showing switching of the transmission characteristics.
Figure 9:
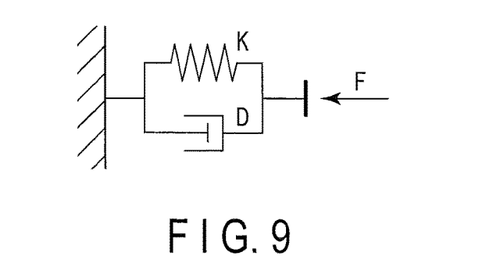
FIG. 9 is a view dynamic-analogically showing a system after switching the transmission characteristics.

Here, in the first embodiment, when it is determined that the torque limit should be applied, the controller 200 is disconnected from the motor 150 by the relay 208. On the other hand, in this embodiment, when it is determined that the torque limit should be applied, the motor control section 2042 sets the transmission characteristics when the motor 150 is seen from the base tube 132 as such low-pass filter characteristics as shown in FIG. 8B, and performs the PI speed control. When the transmission characteristics are switched to the low-pass filter characteristics, a system when the motor 150 is seen from the base tube 132 operates with the same characteristics as those of a machine having a spring with a spring constant K and a damper with a damping constant D such as shown in FIG. 9.

Figure 10:
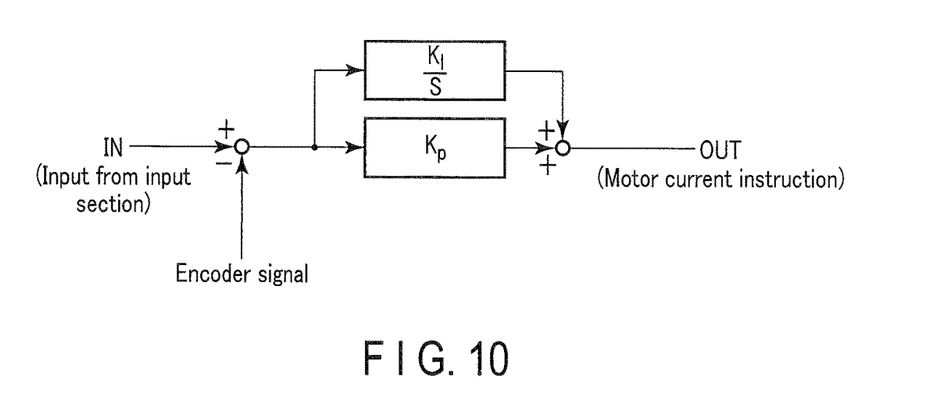
FIG. 10 is a block diagram showing a function of a motor control section.

The transmission characteristics are switched by switching a proportional gain and an integration gain in the motor control section 2042. FIG. 10 is a block diagram showing a function of the motor control section 2042. As shown in FIG.10, the motor control section 2042 is configured to output, as an instruction signal of a motor current, a sum of products obtained by multiplying an instruction signal from an input section 360 and a difference signal from an incremental encoder 152 by a proportional gain Kp and multiplying the same by an integration gain KI/s (s is a Laplace operator). In such a configuration, in a case where the torque limit is not applied, a proportional gain KPn and an integration gain KIn to set transmission characteristics when the torque limit is not applied, i.e., when (2) is seen from(1) in FIG. 7 as the low-pass characteristics are used. On the other hand, in a case where the torque limit is applied, a proportional gain KPt and an integration gain KIt to set the transmission characteristics when (2) is seen from (1) in FIG. 7 as the low-pass filter characteristics are used. These proportional gain and integration gain are stored in the motor control section 2042 in advance.

Figure 11:
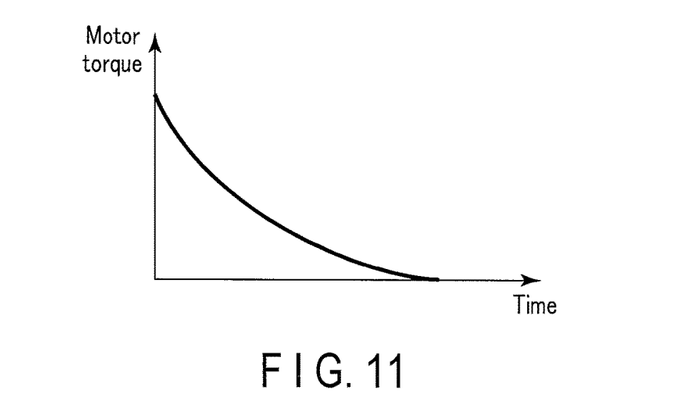
FIG. 11 is a view showing a damping behavior of the torque when a torque limit is applied.

With such switching of the transmission characteristics, a damping behavior of torque when the torque limit is applied has such characteristics as shown in FIG. 11. That is, the characteristics in FIG. 11 are characteristics that the torque is sequentially reduced with time and the torque becomes zero, namely, the motor 150 is stopped at a given time point. It is to be noted that a time constant of a damping curve in FIG. 11 is represented by the following Expression. It is to be noted that s in the following expression is the Laplace operator. Furthermore, K is a spring constant. D is a damping constant.

$$\frac{K}{s+D}$$

As described above, according to this embodiment, the low-pass filter characteristics are adopted as the transmission characteristics when the motor 150 is seen from the base tube 132 by switching the transmission characteristics provided by the motor control section 2042. Consequently, for example, external force F provided by a counteraction from a lumen in a situation where the spiral fin 134 is in contact with the lumen is absorbed by behavior of the motor 150 or the like which is to have spring/damper characteristic. In this manner, like the first embodiment, the force given to the lumen can be eliminated.

Further, since the motor 150 is not free like the first embodiment, unnecessary regenerative power caused due to rotation of the motor 150 after freeing the motor 150 like the first embodiment is not produced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an inserting section formed along a longitudinal axis extending from a proximal end side towards a distal end side;
   a rotary cylinder configured to be rotatable around the longitudinal axis of the inserting section, wherein the rotary cylinder comprises a spiral fin spirally provided along the longitudinal axis of the inserting section;
   a motor configured to rotate the rotary cylinder;
   a motor control section configured to supply a motor current to drive the motor, and to control driving of the motor;
   a moving average calculating section configured to calculate an average of the motor current within a predetermined period from after the motor starts up; and
   a torque limit determining section configured to, when at a time of startup of the motor, determine whether torque of the motor is in a limit state by comparing a calculating result of the moving average calculating section with a predetermined torque limit set value, and, when not at a time of startup of the motor, does not determine whether the torque of the motor is in the limit state.

2. The apparatus according to claim 1, further comprising a relay provided between the motor control section and the motor,
   wherein the motor control section is configured to stop the motor by using the relay to interrupt supply of the motor current to the motor, when the average of the motor current is determined to exceed the torque limit set value.

3. The apparatus according to claim 2, further comprising an input section configured to give an instruction to drive the motor, wherein the motor control section is configured to control to start up the motor when the input section gives the instruction to drive the motor after the motor is stopped.

4. The apparatus according to claim 1,
wherein the motor control section is configured to stop the motor by switching control of driving of the motor so that transmission characteristics when the motor is seen from the rotary cylinder are set as low-pass filter characteristics, when the average of the motor current is determined to exceed the torque limit set value.

* * * * *